United States Patent
Freund et al.

(10) Patent No.: US 12,286,412 B2
(45) Date of Patent: *Apr. 29, 2025

(54) HETEROCYCLIC RED AZO COLORANTS FOR SEED TREATMENT APPLICATIONS

(71) Applicant: Milliken & Company, Spartanburg, SC (US)

(72) Inventors: Wesley A. Freund, Simpsonville, SC (US); Innus Mohammad, Spartanburg, SC (US)

(73) Assignee: Milliken & Company, Spartanburg, SC (US)

( * ) Notice: Subject to any disclaimer, the term of this patent is extended or adjusted under 35 U.S.C. 154(b) by 360 days.

This patent is subject to a terminal disclaimer.

(21) Appl. No.: 17/714,298

(22) Filed: Apr. 6, 2022

(65) Prior Publication Data

US 2022/0411387 A1  Dec. 29, 2022

Related U.S. Application Data

(60) Provisional application No. 63/208,996, filed on Jun. 10, 2021.

(51) Int. Cl.
| | | |
|---|---|---|
| *C07D 277/82* | (2006.01) | |
| *C09B 29/36* | (2006.01) | |
| *G01N 21/78* | (2006.01) | |

(52) U.S. Cl.
CPC ........ *C07D 277/82* (2013.01); *C09B 29/3691* (2013.01); *G01N 21/78* (2013.01)

(58) Field of Classification Search
CPC .............. C07D 277/82; C09B 29/3691; C09B 29/0085; C09B 29/0088; C09B 29/0813; C09B 67/0083; A01C 1/06
See application file for complete search history.

(56) References Cited

U.S. PATENT DOCUMENTS

| | | | |
|---|---|---|---|
| 4,640,690 | A | 2/1987 | Baumgartner |
| 4,732,570 | A | 3/1988 | Baumgartner |
| 4,758,243 | A | 7/1988 | Rekers |
| 4,978,362 | A | 12/1990 | Kluger |
| 5,043,013 | A | 8/1991 | Kluger |
| 5,240,980 | A | 8/1993 | Danielson |
| 6,764,541 | B1 | 7/2004 | Banning |
| 2006/0074142 | A1 | 4/2006 | Banning |

FOREIGN PATENT DOCUMENTS

| | | | | |
|---|---|---|---|---|
| CN | 101403694 | A | 4/2009 | |
| EP | 0437105 | A1 | 7/1991 | |
| EP | 0604222 | A1 | 6/1994 | |
| EP | 0789987 | A1 | 8/1997 | |
| JP | 3113037 | B2 | 11/2000 | |
| TW | 202100669 | A | 1/2021 | |
| WO | WO 2022/056205 | A1 * | 3/2022 | ............... A61Q 5/06 |

OTHER PUBLICATIONS

International Search Report and Written Opinion issued in App. No. PCT/US2022/027292, mailing date Sep. 2, 2022, 18 pages.

* cited by examiner

*Primary Examiner* — Alicia L Otton
*Assistant Examiner* — David M Shim
(74) *Attorney, Agent, or Firm* — Brenda D. Amidon

(57) ABSTRACT

This invention relates to heterocyclic red azo colorants for seed treatment applications. The red azo colorants contain a heterocycle that includes one nitrogen atom and one sulfur atom and are free from electron-withdrawing groups on the heterocycle. Seeds for use in horticultural/agriculture applications that are coated with the heterocyclic azo colorants provide anti-counterfeiting properties to the coated seeds. A color change phenomenon is observed when the coated seeds are exposed to an acidic material, such as vinegar, and provides evidence of the authenticity of the coated seeds. The invention also relates to agricultural formulations containing the heterocyclic red azo colorants that can be used as an anti-counterfeit agents.

15 Claims, No Drawings

HETEROCYCLIC RED AZO COLORANTS FOR SEED TREATMENT APPLICATIONS

CROSS REFERENCE TO RELATED APPLICATIONS

This application claims priority to U.S. Provisional Patent Application No. 63/208,996, entitled "Heterocyclic Red Azo Colorants For Seed Treatment Applications," which was filed on Jun. 10, 2021, and is entirely incorporated by reference herein.

TECHNICAL FIELD

This invention relates to heterocyclic red azo colorants for seed treatment applications. The red azo colorants contain a heterocycle that includes one nitrogen atom and one sulfur atom and are free from electron-withdrawing groups on the heterocycle. Seeds for use in horticultural/agriculture applications that are coated with the heterocyclic azo colorants provide anti-counterfeiting properties to the coated seeds. A color change phenomenon is observed when the coated seeds are exposed to an acidic material, such as vinegar, and provides evidence of the authenticity of the coated seeds. The invention also relates to the use of these heterocyclic red azo colorants as anti-counterfeit agents in agricultural formulations.

BACKGROUND

Seed security is of prime importance for agriculture. There are markets throughout the world where fake or forged seeds may flood the market. These fake seeds may be of inferior quality. In order to protect their image, seed companies need to have the ability to differentiate their seeds from others that may be trying to mimic their brand. Additionally, farmers should have the tools available to determine if the seed they purchased is an authentic seed and will yield the quality crop that they expect from their investment.

In addition to counterfeit seeds, agricultural formulations that contain one or more agricultural active ingredients that are not authentic could also be introduced into the market. In order to authenticate the agricultural formulation, a clear indicator test is needed. The use of counterfeit agricultural formulations could result in crop damage or crop loss for a farmer. This, in turn, could also cause damage to the reputation of the agricultural suppliers.

There are only a few technologies presented in the literature to address counterfeit seeds and agricultural formulations. However, the majority of them rely on the use of fluorescent dyes. For example, CN101403694A discloses a fluorescence anti-counterfeit and detection method for pelleted seed. For these inventions to work, the seeds must be put under a UV light source to be able to observe the fluorescence effect. This is not always easy to do in the field where seed use is manifested. As such, there exists a need for a technology that allows for an easy identification of agricultural formulations of active ingredients and the seeds treated with them.

It was found that specific heterocyclic red azo colorants are capable of acting as anti-counterfeit agents for in-can agricultural active ingredient formulations as well as for seeds coated with such formulations. The use of these specific colorants allows for an easy test using readily available household chemicals (such as vinegar and toilet cleaner) to rapidly identify an authentic seed. Current red dyes (such as FD&C Red 40 and FD&C Red 33) and red pigments (such as pigment red 48:2 and pigment red 112), which are available and approved for use as seed treatments/coatings in the United States do not offer the same visual change in the presence of acidic substances as exhibited by the heterocyclic azo colorants of the present invention. In addition, dyes that are not polymeric, like those presented herein, often suffer from poor coverage in application to seeds and poor coloration. The present invention addresses these shortcomings and offers additional benefits over other types of colorants, such as water solubility, non-staining properties, improved treater buildup and improvements in treater cleanup. Therefore, the heterocyclic red azo colorants of the present invention represent an advancement over the prior art and further fulfill a need that prevents counterfeit agricultural products from being used in the marketplace.

BRIEF SUMMARY

In one aspect, the invention relates to a method for determining the authenticity of a seed or an agricultural formulation comprising the following steps: (a) providing a seed or an agricultural formulation that contains a red azo colorant represented by the following formula:

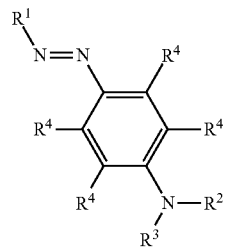

wherein $R^1$ comprises at least one 5 membered ring incorporating one N and one S atom within the ring system, and wherein the ring system is free from electron-withdrawing groups; $R^2$ and $R^3$ are independently selected from the group consisting of H, alkyl, and poly(oxyalkylene) moieties, wherein at least one of $R^2$ and $R^3$ is a poly(oxyalkylene) moiety; and $R^4$ is independently selected from the group consisting of H, alkyl, substituted alkyl, nitrogen, substituted nitrogen, oxygen, halogens and ethers; (b) adding an acidic material to the seed or agricultural formulation of step "a;" and (c) visually observing the occurrence of a color change from red to violet with the addition of the acidic material.

In another aspect, the invention relates to a composition comprising: (a) an agricultural formulation that includes at least one agricultural active ingredient, and (b) at least one red azo colorant represented by the following formula:

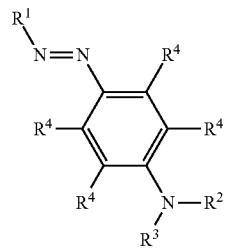

wherein $R^1$ comprises at least one 5 membered ring incorporating one N and one S atom within the ring system, and wherein the ring system is free from electron-withdrawing groups; $R^2$ and $R^3$ are independently selected from the group consisting of H, alkyl, and poly(oxyalkylene) moieties, wherein at least one of $R^2$ and $R^3$ is a poly(oxyalkylene) moiety; and $R^4$ is independently selected from the group consisting of H, alkyl, substituted alkyl, nitrogen, substituted nitrogen, oxygen, halogens and ethers.

In a further aspect, the invention relates to a composition comprising: (a) an agricultural formulation that contains at least one agricultural active ingredient, and (b) at least one red azo colorant selected from Formulas I and II:

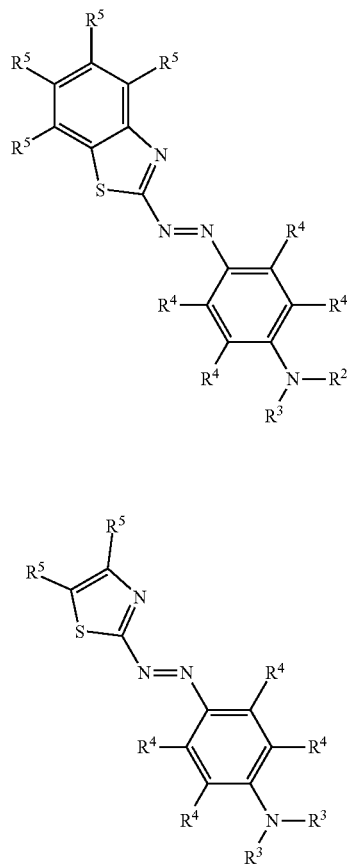

wherein $R^2$ and $R^3$ are independently selected from the group consisting of H, alkyl, and poly(oxyalkylene) moieties, wherein at least one of $R^2$ and $R^3$ is a poly(oxyalkylene) moiety; $R^4$ is independently selected from the group consisting of H, alkyl, substituted alkyl, nitrogen, substituted nitrogen, oxygen, halogens and ethers; and $R^5$ is independently selected from the group consisting H, alkyl, substituted alkyl, hydroxyl, substituted hydroxyl, aryl, and substituted aryl.

In yet another aspect, the invention relates to a composition comprising: (a) an agricultural formulation comprising at least one agricultural active ingredient, and (b) at least one red azo colorant represented by Formula III:

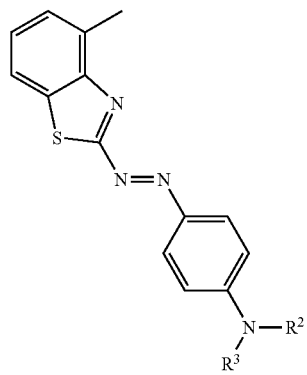

wherein $R^2$ and $R^3$ are independently selected from the group consisting of H, alkyl, and poly(oxyalkylene) moieties, and wherein at least one of $R^2$ and $R^3$ is a poly(oxyalkylene) moiety.

In another aspect, the invention relates to a composition comprising: (a) an agricultural formulation comprising at least one agricultural active ingredient, and (b) a red azo colorant represented by Formula IV:

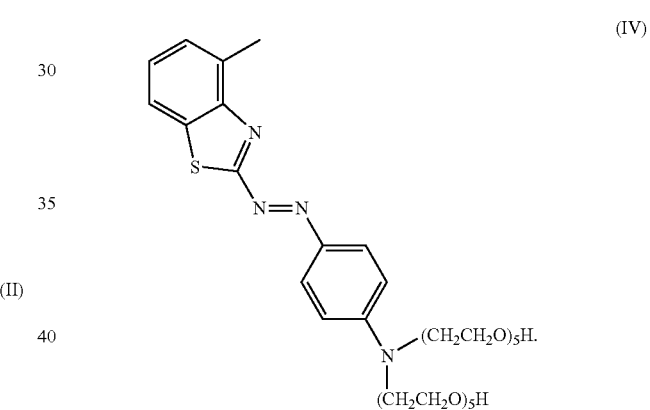

DETAILED DESCRIPTION

The present invention relates to red azo colorants that contain a heterocycle composed of at least one nitrogen atom and one sulfur atom and are free from electron-withdrawing groups on the heterocycle. The select colorants are capable of providing anti-counterfeiting properties to seeds coated therewith. The invention further includes seeds coated with the heterocyclic azo colorants described herein.

In addition, the select colorants are capable of providing anti-counterfeiting properties to an agricultural active ingredient or polymer formulation containing the heterocyclic azo colorants as described herein.

The anti-counterfeiting property of the seeds coated with the heterocyclic colorants of the present invention is evaluated using common household items that are acidic in nature and having a having a pH When exposed to an acidic substance at a pH (such as vinegar or toilet bowl cleaner containing muriatic acid), the coated seeds will exhibit a shift in the shade of the colorant from a red to a violet color. This test can be used to identify that the colorant on the seed is authentic and can be used as a marker for the seed or agricultural formulation, preventing counterfeit formulations or seeds from being sold and/or marketed.

As used herein, the term "heterocycle" and "heterocyclic" is intended to describe/include a cyclic compound that contains at least one heteroatom in the ring system. Examples of heterocycles include, without limitation, thiazole, benzothiazole, imidazole, thiophene, furan, benzofuran, thiadiazole, oxazole, isoxazole, oxadiazole, benzoxazole, triazole, and pyridyl.

As used herein, the term "electron-withdrawing groups" is intended to include an atom or group that draws electron density from neighboring atoms towards itself, usually by resonance or inductive effects. Some examples of electron-withdrawing groups can include halogen, sulfonate, carboxylic acid, ester, ketone, aldehyde, nitrile, amide, phosphate and nitro groups.

As used herein, the term "alkoxy" is intended to include $C_1$-$C_8$ alkoxy and alkoxy derivatives of polyols having repeating units such as butylene oxide, glycidol oxide, ethylene oxide or propylene oxide.

As used herein, unless otherwise specified, the terms "alkyl" and "alkyl capped" are intended to include $C_1$ to $C_{100}$ alkyl groups, $C_1$ to $C_{50}$ alkyl groups, $C_5$ to $C_{25}$ alkyl groups, or even $C_{10}$ to $C_{20}$ alkyl groups.

As used herein, unless otherwise specified, the term "aryl" is intended to include $C_6$ to $C_{12}$ aryl groups.

As used herein, unless otherwise specified, the term "arylalkyl" is intended to include $C_1$ to $C_{18}$ alkyl groups and, in one aspect, $C_1$ to $C_6$ alkyl groups.

In one aspect, the invention relates to the use of poly (oxyalkylene) substituted red azo colorants in seed coating applications where the colorant is mixed with an agricultural formulation that contains at least one agricultural active ingredient (such as a pesticide, which includes without limitation, a fungicide, an insecticide, a nematocide, and the like) and applied directly to a seed surface. Seeds include, without limitation, row crops (corn, soybeans, etc.), grass seeds, or any other type of seed that would be treated directly with an agricultural formulation.

In another aspect, the invention relates to the use of poly(oxyalkylene) substituted red azo colorants in agricultural formulations containing at least one agricultural active ingredient wherein the agricultural formulation is colored with the poly(oxyalkylene) substituted red azo colorants.

The colorant of the present invention is represented by the following formula:

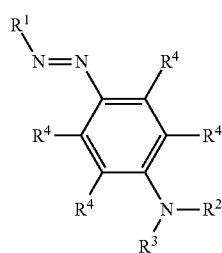

wherein $R^1$ comprises at least one 5 membered ring incorporating one N and one S atom within the ring system, and wherein the ring system is free from electron-withdrawing groups;

$R^2$ and $R^3$ are independently selected from the group consisting of H, alkyl, and poly(oxyalkylene) moieties, wherein at least one of $R^2$ and $R^3$ is a poly(oxyalkylene) moiety; and $R^4$ is independently selected from the group consisting of H, alkyl, substituted alkyl, nitrogen, substituted nitrogen, oxygen, halogens and ethers.

In one aspect of the invention, $R^1$ may be further selected from the group consisting of thiazole, isothiazole, benzisothiazole, and benzothiazole. $R^1$ may preferably be selected from thiazole and benzothiazole. The heterocyclic ring(s) $R^1$ may additionally include various substituents on the ring(s) selected from the group consisting of H, alkyl, substituted alkyl, hydroxyl, substituted hydroxyl, aryl, substituted aryl, and the like, provided the substituents are not considered electron-withdrawing groups.

Poly(oxyalkylene) moieties include, for instance, ethylene oxide (EO; a/k/a ethyleneoxy), propylene oxide (PO; a/k/a propyleneoxy), butylene oxide (BO; a/k/a butyleneoxy), and combinations thereof. The total number of alkylene oxide residues per colorant molecule ranges from 4 to 250, preferably 5 to 100, with 5 to 20 representing an optimum for fugitivity, viscosity and color strength.

Examples of the azo chromophore groups suitable for use in the present invention include monoazos, disazos, trisazos, tetrakisazos, polyazos, formazans, azomethines and metal complexes thereof.

The heterocyclic azo red colorant may be present in the seed coating in an amount ranging from about 0.001% to about 50% by weight of the coating, or even from about 0.5% to about 10% by weight of the coating.

The heterocyclic azo red colorant may be present in an agricultural formulation in an amount ranging from about 0.001% to about 50% by weight of the formulation, or even from about 0.5% to about 10% by weight of the formulation.

The synthesis of the heterocyclic azo colorants includes the reaction of an aromatic amine with nitrous acid to form a diazonium salt. This diazonium salt is then coupled to a suitable coupler to form an azo bond. Preferred aromatic amines are those that contain a thiazole or benzothiazole ring system. Preferred couplers are alkoxylated aniline derivatives.

In another aspect of the invention, the seed coating composition includes at least one heterocyclic azo colorant and at least one agricultural active ingredient. An "agricultural active ingredient" will exert a biologically relevant effect on the seed or plant. For example, the agricultural active ingredient may exert a pesticidal effect. Alternatively, the agricultural active ingredient may function to provide nutrition or control one or more plant diseases.

Some examples of agricultural active ingredients include, but are not limited to fungicidal agents, insecticidal agents, nematicidal agents, biological agents, pesticides, and biocides. Additional agricultural active ingredients could also consist of rodent killers, weed killers, plant growth regulators, plant growth stimulators, nutrients, hormones, and the like. Any combination of the foregoing may also be used as agricultural active ingredients.

The recommended dosing rates of agricultural active ingredients vary due to application, seed type, specific active ingredient used and desired outcome. Agricultural active ingredients can be blended to together within the same seed treatment formulation. Typically, the amount of one or more agricultural active ingredients is in the range from about 0.001 to about 200 g per kg of the seed. One skilled in the art is able to determine suitable amounts of agricultural active ingredient depending on the active ingredient and the type of seed used. Technical data sheets or active ingredient labels available from the suppliers of those ingredients will also provide additional guidance.

The following is a list of agricultural active ingredients which may be used in a seed coating composition as described herein and is intended to further illustrate possible active ingredients, but not to impose any limitation.

Non-limiting commercial examples of fungicidal ingredients include metalaxyl (available from Bayer under the tradename Allegiance®-FL), Fludioxonil (commercially available from Syngenta under the tradename Maxim® 4FS), tebuconazole, thiabendazole, azoxystrobin, and the like.

Non-limiting examples of commercially available insecticides include thiomethoxam (from Syngenta under the tradename Cruiser®), Chlorantraniliprole (available from Dupont under the tradename Lumivia™), fipronil (from BASF under the tradename Regent®), imidacloprid, clothianidin (from Bayer under the tradename Ponche), and the like.

Non-limiting examples of commercially available nematicidal ingredients include abamectin (available from Syngenta under the tradename Avicta®), *Bacillus amyloliquefaciens* strain PTA-4838 (available from Valent under the tradename Aveo™ EZ Nematicide), thiodicarb (available from Bayer under the tradename Aeris®), and the like.

One or more additional components may be optionally included in the seed coating composition of the present invention. These additional components may be selected from binders, waxes, coloring agents, thickeners, dispersants, surfactants, anti-foam agents, anti-freeze agents, bactericidal agents, solvents or combinations thereof. One or more of these additional components may be present in the seed coating composition in an amount ranging from about 0.001% to about 50% by weight of the coating.

The seed coating composition may include a binder or a film-forming polymer. The binder can be any suitable binder approved for agricultural use. One such list of suitable binders can be found in the U.S. Code of Federal Regulations Title 40, Part 180.960, which is entirely incorporated by reference herein.

The binder may be a polymer selected from the group consisting of vinyl acetate-ethylene copolymer, vinyl acetate homopolymer, vinyl acetate-acrylic copolymer, vinylacrylic, acrylic, ethylene-vinyl chloride, vinyl ether maleic anhydride, and butadiene styrene, and the like, and combinations thereof.

Included in this list of suitable binders are acrylic polymers comprised of one or more of the following monomers: acrylic acid, methyl acrylate, ethyl acrylate, butyl acrylate, hydroxy-ethyl acrylate hydroxybutyl acrylate, carboxyethyl acrylate, methacrylic acid, methyl methacrylate, hydroxy butyl meth-acrylate, lauryl methacrylate, and stearyl methacrylate; with none and/or one or more of the following monomers: acryla-mide, N-methyl crylamide, N,N-dimethyl acrylamide, N-octyl acrylamide, maleic anhydride, maleic acid, monoet-35 hyl maleate, diethyl maleate, monooctyl maleate, dioctyl maleate; and their corresponding sodium, potassium, ammo-nium, isopropylamine, triethylamine, monoethanolamine, and/or triethanolamine salts. Other suitable binders from this list include: copolymers of methyl vinyl ether with maleic anhydride or monoalkyl esters of maleic anhydride (e.g. Agrimer® VEMA line of products from ISP); polyvinylpyr-rolidone; copolymers of vinyl pyrrolidone with vinyl acetate (e.g., Agrimer VA line of products from ISP); copolymers of vinyl pyrrolidone with vinyl alkyls (e.g. Agrimer® AL line of 45 products from ISP); polyvinyl acetate; ethylene/vinyl acetate copolymers (e.g. Atlox® SemKote E product line from Uniqema); vinyl acetate acrylic copolymers (e.g., Atlox® Semkote V product line from Uniqema); A-B block copoly-mers of ethylene oxide and propylene oxide; A-B-A triblock 50 copolymers of EO-PO-EO (e.g. Pluronics® line from BASF); and polyvinyl alcohol.

Examples of suitable waxes include polyethylene wax, polypropylene wax, carnauba wax, Fischer-Tropsch wax, paraffin wax, triglycerides, metal soaps, and combinations thereof.

Suitable surfactants including dispersants or emulsifiers, are alkali metal, alkaline earth metal and ammonium salts of aromatic sulfonic acids, such as ligninsoulfonic acid (Borresperse® types, Borregard, Norway) phenolsulfonic acid, naphthalenesulfonic acid (Morwet® types, Akzo Nobel, U.S.A.), dibutylnaphthalenesulfonic acid (Nekal® types, BASF, Germany), and fatty acids, alkylsulfonates, alkylarylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, tristearylphenyl polyglycol ether, alkylaryl polyether alcohols, alcohol and fatty alcohol/ethylene oxide condensates, ethoxylated castor oil, polyoxyethylene alkyl ethers, lauryl alcohol polyglycol ether acetal, sorbitol esters, maleic anhydride-diisobutylene copolymer, polyvinyl alcohols (Mowiol® types, Clariant, Switzerland), polycarboxylates (Sokolan® types, BASF, Germany), and polyalkoxylates.

Examples of thickeners are polysaccharides and organic and inorganic clays such as attapulgite clay, bentonite clay, smectite clay, hectorite clay, cellulosic, xanthan gum, or guar gum. Preferred thickeners are xanthan gum (Kelzan®, C P Kelco, U.S.A.).

Bactericides may be added for preservation and stabilization of the composition. Some examples of suitable bactericides are those based on isothiazolinone derivatives such as benzisothiazolinone (BIT), methylisothiazolinone (MIT), chloromethylisothiazolinone (OMIT), and combinations thereof. Suitable bactericides are commercially available from Thor under the Acticide® tradename.

Examples of suitable anti-freeze agents are ethylene glycol, propylene glycol, urea and glycerin. A preferred example of an anti-freeze agent is propylene glycol.

Examples of anti-foam agents are silicone emulsions, long chain alcohols, fatty acids, salts of fatty acids, and mixtures thereof.

Additional coloring agents may be blended with the inventive colorants. Preferred additional coloring agents are pigments of low water solubility and water-soluble dyes. Non-limiting examples of coloring agents include Milliken Blue 5200, acid blue 9, pigment blue 15, C.I. pigment blue 29, pigment violet 23, pigment yellow 1, acid yellow 23, pigment red 112, pigment red 48:2, pigment red 48:1, acid red 33, food red 17, pigment green 7, solvent green 3, pigment white 6, carbon black, pearlescent pigment which consists of mica platelets coated with titanium dioxide and/or iron oxide, and combinations thereof.

Preferably, the seed coating composition is applied as an aqueous composition and thereafter solidified (including cured and/or dried) to form a seed coating. The total coating composition can be in the form of a suspension, solution, emulsion, or dispersion. The pH of the coating composition can range from pH=3-12, preferably from pH=5-10, and most preferably from pH=6-9. For the present invention to function properly as an anti-counterfeit agent, the pH of the seed coating composition should be greater than 3.

In one aspect of the invention, all components of the seed coating composition are blended and mixed together at room temperature until homogenized into a slurry prior to their application onto the seeds. Alternatively, the various components of the formulation may be dosed separately in stages to the seed during the seed treatment/seed coating process. Conventional means of coating may be employed for coating the seeds. Various coating machines are available to the person skilled in the art. Some common techniques include the use of drum coaters, rotary coaters, and fluidized bed techniques. The coating may be air dried or heat dried on the seed prior to packaging.

Typically, the amount of seed coating composition applied to the seed can be in the range of 0.5-50 g per kg seed, or even 1-40 g per kg seed, or 2-35 g per kg seed, or 3-30 g per kg seed.

In a further aspect, the present invention includes a composition comprising:

(a) An agricultural formulation that includes at least one agricultural active ingredient, and (b) At least one red azo colorant represented by the following formula:

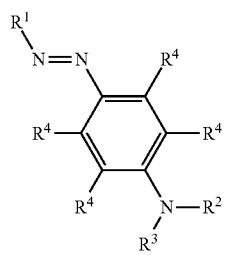

wherein $R^1$ comprises at least one 5 membered ring incorporating one N and one S atom within the ring system, and wherein the ring system is free from electron-withdrawing groups;

$R^2$ and $R^3$ are independently selected from the group consisting of H, alkyl, and poly(oxyalkylene) moieties, wherein at least one of $R^2$ and $R^3$ is a poly(oxyalkylene) moiety; and $R^4$ is independently selected from the group consisting of H, alkyl, substituted alkyl, nitrogen, substituted nitrogen, oxygen, halogens and ethers.

The agricultural formulation is present in the composition in an amount in the range from 95% to 99.999%. The at least one red azo colorant is present in the composition in an amount in the range from 0.001% to 95%.

The invention further includes a seed coated with this composition that comprises an agricultural formulation and at least one red azo colorant.

The composition may further include at least one of a polymeric binder and a film-forming polymer as described herein.

The invention also encompasses a composition comprising:

(a) An agricultural formulation that contains at least one agricultural active ingredient, and (b) At least one red azo colorant selected from Formulas I and II:

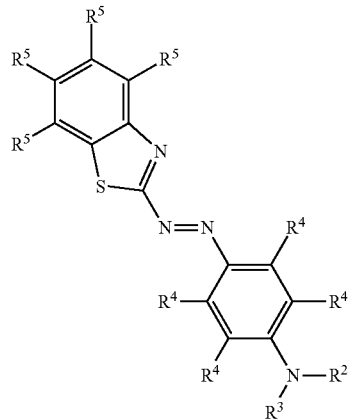

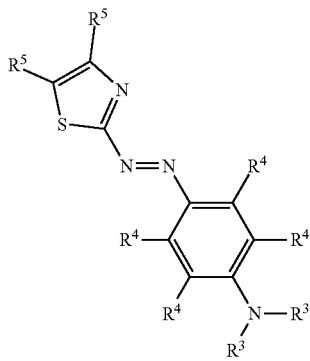

wherein $R^2$ and $R^3$ are independently selected from the group consisting of H, alkyl, and poly(oxyalkylene) moieties, wherein at least one of $R^2$ and $R^3$ is a poly(oxyalkylene) moiety;

$R^4$ is independently selected from the group consisting of H, alkyl, substituted alkyl, nitrogen, substituted nitrogen, oxygen, halogens and ethers; and $R^5$ is independently selected from the group consisting H, alkyl, substituted alkyl, hydroxyl, substituted hydroxyl, aryl, and substituted aryl.

In the composition, the total number of alkylene oxide residues per colorant molecule is in the range from 5 to 20. The invention further includes a seed coated with this composition that comprises an agricultural formulation and at least one red azo colorant of Formula I and Formula II.

Also encompassed in the invention is a composition comprising:

(a) An agricultural formulation comprising at least one agricultural active ingredient, and (b) At least one red azo colorant represented by Formula III:

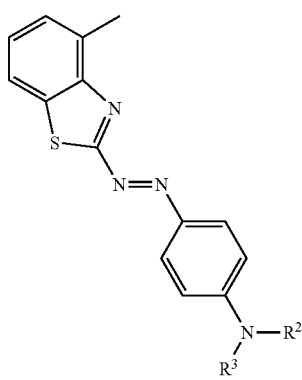
(III)

wherein $R^2$ and $R^3$ are independently selected from the group consisting of H, alkyl, and poly(oxyalkylene) moieties, and wherein at least one of $R^2$ and $R^3$ is a poly(oxyalkylene) moiety.

The invention further includes a seed coated with this composition that comprises an agricultural formulation and at least one red azo colorant represented by Formula III.

Additionally, the invention includes a composition comprising:

(a) An agricultural formulation comprising at least one agricultural active ingredient, and (b) A red azo colorant represented by Formula IV:

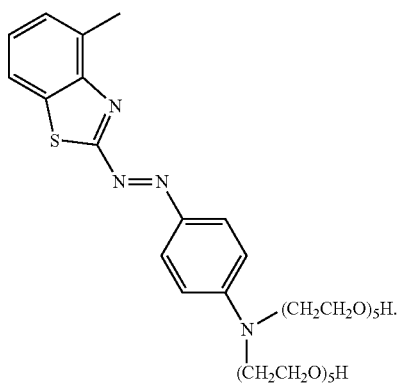
(IV)

The invention further includes a seed coated with this composition that comprises an agricultural formulation and at least one red azo colorant represented by Formula IV.

As discussed previously, the red azo colorant of the present invention is useful for determining the authenticity of a seed coated with the colorant or of an agricultural formulation containing the red azo colorant. One method for determining the authenticity of a seed or an agricultural formulation comprises the following steps:

(a) Providing a seed or an agricultural formulation that contains a red azo colorant represented by the following formula:

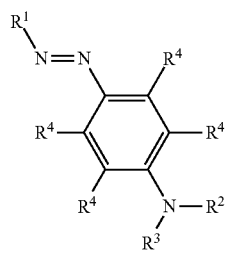

wherein $R^1$ comprises at least one 5 membered ring incorporating one N and one S atom within the ring system, and wherein the ring system is free from electron-withdrawing groups;

$R^2$ and $R^3$ are independently selected from the group consisting of H, alkyl, and poly(oxyalkylene) moieties, wherein at least one of $R^2$ and $R^3$ is a poly(oxyalkylene) moiety; and $R^4$ is independently selected from the group consisting of H, alkyl, substituted alkyl, nitrogen, substituted nitrogen, oxygen, halogens and ethers;

(b) Adding an acidic material to the seed or agricultural formulation of step "a;"

(c) Visually observing the occurrence of a color change from red to violet with the addition of the acidic material.

The acidic material generally has a pH 3. Further features of the method include wherein the seed of step "a" is placed in an aqueous solution prior to the addition of the acidic material. The red azo colorant may be present in a coating on the seed when placed into the solution. The red azo colorant of step "a" may be present in an amount ranging from about 0.001% to about 50% by weight of the coating, or even in an amount ranging from about 0.5% to about 10% by weight of the coating.

In a further method of the invention, the red azo colorant of step "a" may be represented by Formula I or Formula II:

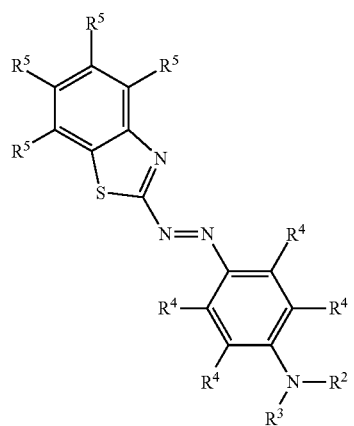
(I)

-continued

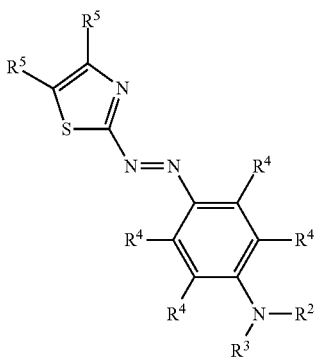

(II)

wherein:

R² and R³ are independently selected from the group consisting of H, alkyl, and poly(oxyalkylene) moieties, and wherein at least one of R² and R³ is a poly(oxyalkylene) moiety;

R⁴ is independently selected from the group consisting of H, alkyl, substituted alkyl, nitrogen, substituted nitrogen, oxygen, halogens and ethers; and R⁵ is independently selected from the group consisting H, alkyl, substituted alkyl, hydroxyl, substituted hydroxyl, aryl, and substituted aryl.

In another method of the invention, the red azo colorant of step "a" is represented by Formula III:

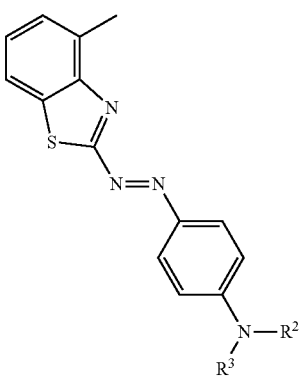

(III)

wherein R² and R³ are independently selected from the group consisting of H, alkyl, and poly(oxyalkylene) moieties, and wherein at least one of R² and R³ is a poly(oxyalkylene) moiety.

In another alternative method of the invention, the red azo colorant of step "a" is represented by Formula IV:

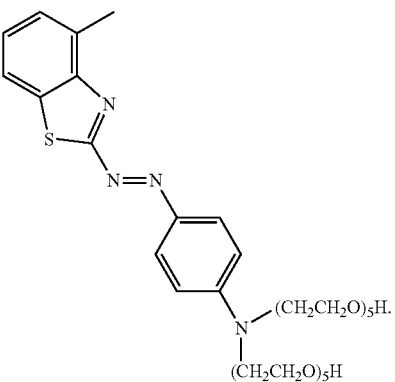

(IV)

Also encompassed within this invention is a kit and/or system for determining the authenticity of a seed or an agricultural formulation. The kit and/or system comprises the following components: (1) a seed coated with the red azo colorant as described in all its various forms herein or an agricultural formulation containing said red azo colorant and (2) an acidic material of pH≤3.

EXAMPLES

The following Examples are provided for illustration purposes and should not be considered as limiting the scope of the invention. These examples are intended to demonstrate the preparation and anti-counterfeiting property of the heterocyclic red azo colorants of the current invention.

Inventive Example 1

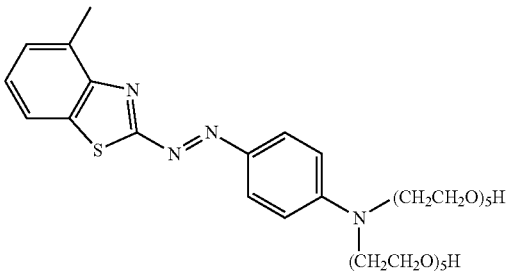

The diazo solution was prepared by charging 50 grams (g) of 2-amino-4-methylbenzothiazole and 500 g of 85% phosphoric acid into a 1000 mL round bottom flask. Once the diazo solution mixture was cooled to −5° C.-0° C., 24.29 g of sodium nitrite was added slowly over 30 minutes. The diazo solution was then stirred vigorously for 2.5 hours maintaining −5° C.-0° C. Sulfamic acid was added to the diazo solution to destroy excess nitrous acid. A separate 2000 mL round bottom flask was charged with 178.73 g of aniline 10EO (10 moles of ethylene oxide polymerized off of the aniline nitrogen) and 650 g of water. The solution was cooled to 0° C. The diazo solution was then added slowly to the aniline 10EO mixture maintaining a temperature from 0-10° C. The resulting mixture was then stirred for one hour under 0-10° C. and then the ice bath was removed. The solution was then neutralized to a pH of 7 using 50% sodium hydroxide and heated to 70° C. The neutralized mixture was then added to a separatory funnel and placed in a 70° C. oven overnight. The water layer was separated, and the red product was recovered.

Inventive Example 2

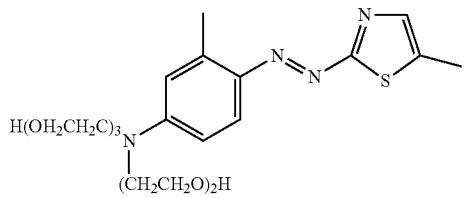

The diazo solution was prepared by charging 80 g of 2-amino-5-methylthiazole, 400 g of water and 204 g of sulfuric acid to a 1 L round bottom flask. The contents were cooled to 0° C.-5° C. 52.8 g of sodium nitrite was dissolved in 160 g of water and slowly added to the round bottom flask maintaining 0° C.-5° C. This solution was then stirred for 1 hour at 0° C.-5° C., after which excess nitrous acid was destroyed with the addition of sulfamic acid. A separate 2 L beaker was charged with 252 g of m-toluidine 5EO and 400 g of water and was cooled to 0° C.-5° C. The diazo solution was then slowly added to the 2 L beaker containing the m-toluidine 5EO maintaining a temperature of 0° C.-5° C. The resulting solution temperature was held for 30 minutes after which the solution was allowed to warm slowly to room temperature over 1 hour. The solution was then neutralized to a pH of 7 using 50% sodium hydroxide. Once neutralized the solution was added to a separatory funnel and placed in a 70° C. oven for 3 hours. The water layer was separated, and the red product was recovered.

Comparative Example 1

The diazo solution was prepared by charging 5 g of 2-amino-5-chlorothiazole hydrochloride and 100 g of 85% phosphoric acid to a 250 mL round bottom flask and cooled to −5° C.-0° C. To the diazo solution 9.70 g of 40 wt % nitrosyl sulfuric acid in sulfuric acid was added dropwise and stirred for 1 hour at −5° C.-0° C. Sulfamic acid and urea were added to destroy excess nitrous acid. A separate 250 mL round bottom flask was charged with 17.78 g of aniline 10EO and 25 g of water. This solution was cooled to 0° C.-5° C. The diazo solution was then slowly added to the aniline 10EO solution keeping temperature at 0° C.-5° C. The resulting solution temperature was held for 60 minutes after which the solution was allowed to warm slowly to room temperature. The solution was then neutralized to a pH of 7 using 50% sodium hydroxide. Once neutralized the solution was added to a separatory funnel and placed in a 70° C. oven for 3 hours. The water layer was separated, and the red product was recovered.

Comparative Example 2

2-amino-5-bromothiazole hydrobromide was converted to the freebase by combining 5 g of 2-amino-5-bromothiazole hydrobromide, 4.23 g of sodium bicarbonate and 50 mL of water to a 100 mL round bottom flask. The contents were stirred for several hours. The solid was then filtered using vacuum filtration and dried in a vacuum oven overnight at room temperature. A diazo solution was prepared by charging 2 g of 2-amino-5-bromothiazole (as prepared above) and 58 g of 85% phosphoric acid to a 250 mL round bottom flask and cooled to −5° C.-0° C. To the diazo solution 3.90 g of 40% NSA in sulfuric acid was added dropwise and stirred for 1 hour at <0° C. Sulfamic acid and urea was added to destroy excess nitrous acid. A separate 250 mL round bottom flask was charged with 7.15 g of aniline 10EO and 15 g of water. This solution was cooled to 0° C.-5° C. The diazo solution was then slowly added to the aniline 10 EO solution keeping temperature at 0° C.-5° C. The resulting solution temperature was held for 60 minutes after which the solution was allowed to warm slowly to room temperature. The solution was then neutralized to a pH of 7 using 50% sodium hydroxide. Once neutralized the solution was added to a separatory funnel and placed in a 70° C. oven for 3 hours. The water layer was separated, and the red product was recovered.

Comparative Example 3

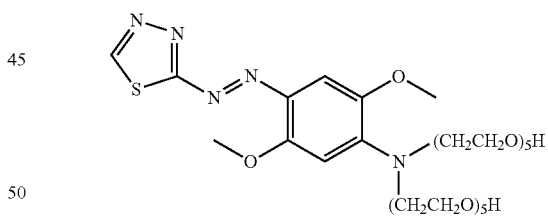

A diazo solution was prepared by combining 3.8 g of 2-amino-1,3,4-thiadiazole with 120 mL of 85% phosphoric acid inside a 250 mL 4-neck round bottom flask equipped with temperature probe, stir shaft, paddle, and guide assembly attached overhead to a mechanical stirrer. The mixture was stirred until a homogenous solution was formed. The reaction mixture was stirred and cooled to −5° C.-0° C. 2.59 g of sodium nitrite was added to the round bottom flask portion wise and the reaction mixture was stirred at 0° C.-5° C. for 1.5 hours. 0.36 g of sulfamic acid was added to the reaction to quench excess nitrous acid, and the reaction was held for 30 minutes at 0° C. A coupler solution was formulated by affixing a 1000 mL 4-neck round bottom flask with a temperature probe, stir shaft, paddle, and guide assembly attached overhead to a mechanical stirrer. This round bottom flask was charged with 22.28 g of 2,5-dimethoxyaniline 10EO and 250 g of water. This mixture was stirred and cooled to below 5° C. The diazo solution was added dropwise to the coupler solution over about 30 minutes, maintaining the temperature below 5° C. The resulting mixture was stirred for 1 hour and allowed to warm to room temperature at which point 250 mL of water was added. 50% sodium hydroxide was added to neutralize excess acid to a pH of about 7 keeping the temperature 35° C.-40° C. The reaction mixture was allowed to phase separate inside a 70° C. oven for 2 hours before the bottom layer was removed and the product layer collected giving a red liquid.

Comparative Example 4

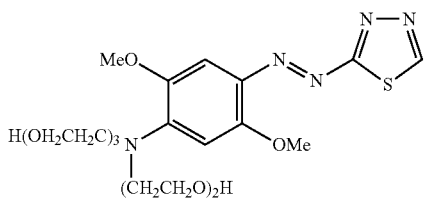

A diazo solution was prepared by combining 7 g of 2-amino-1,3,4-thiadiazole with 202 g of 85% phosphoric acid inside a 250 mL 4-neck round bottom flask equipped with temperature probe, stir shaft, paddle, and guide assembly attached overhead to a mechanical stirrer. The mixture was stirred until a homogenous solution was formed. The reaction mixture was stirred and cooled to −5° C.-0° C. 4.78 g of sodium nitrite was added to the round bottom flask portion wise and the reaction mixture was stirred at 0° C.-5° C. for 1.5 hours. 0.36 g of sulfamic acid was added to the reaction to quench excess nitrous acid, and the reaction was held for 30 minutes at 0° C. A coupler solution was formulated by affixing a 1000 mL 4-neck round bottom flask with a temperature probe, stir shaft, paddle, and guide assembly attached overhead to a mechanical stirrer. This round bottom flask was charged with 25.85 g of 2,5-dimethoxyaniline 5EO and 250 g of water. This mixture was stirred and cooled to 0° C.-5° C. The diazo solution was added dropwise to the coupler solution over about 30 minutes, maintaining the temperature 0° C.-5° C. The resulting mixture was stirred for 1 hour and allowed to warm to room temperature at which point 250 mL of water were added. 50% sodium hydroxide was added to neutralize excess acid to a pH of about 7 keeping the temperature below 40° C. The reaction mixture was allowed to phase separate inside a 70° C. oven for 2 hours before the bottom layer was removed and the product layer collected giving a red liquid.

Test Method for Anti-Counterfeit Colorants in Solution

Samples (10 mg) of colorants to be tested were dissolved in water (10 mL) to obtain a solution. In the case of pigments, a suspension of the pigment was obtained. The color of the water was noted in Table 1. Approximately 1 mL of this water solution was then added to approximately 20 mL of household vinegar (Publix Distilled White Vinegar, 5% acetic acid in water, pH=2.81) and any change in color was noted visually. Test results are shown in Table 1.

TABLE 1

| Anti-Counterfeiting Color Change | | |
|---|---|---|
| Colorant | Colorant in water | Colorant diluted with vinegar |
| Inventive Example 1 | Red | Violet |
| Inventive Example 2 | Red | Violet |
| Comparative Example 1 | Red | Red |
| Comparative Example 2 | Red | Red |
| Comparative Example 3 | Red | Red |
| Comparative Example 4: Pigment Red 112 | Red | Red |
| Comparative Example 5: Pigment Red 48:2 | Pink | Pink |
| Comparative Example 6: FD&C Red 40 | Red | Red |
| Comparative Example 7: D&C Red 33 | Red | Red |

The test results illustrate that Inventive Examples 1 and 2, which contain a thiazole heterocyclic ring with no electron-withdrawing groups on the heterocycle, displayed a visual change in color from red to violet when dissolved in acidic vinegar with a pH of 2.81 vs neutral water, illustrating the anti-counterfeiting property of the present invention. The authenticity of an agricultural formulation (such as a pesticide formulation) that contains these colorants can easily be confirmed by using this test method. The Comparative Examples did not display a color change in the presence of vinegar and thus would not provide a visual cue to authenticate a formulation. Comparative Examples 1 and 2 did not work in the application because they contained an electron-withdrawing group attached to the thiazole moiety. Comparative Examples 4-7 did not work in this application because they did not contain a thiazole heterocycle.

Test Method for Anti-Counterfeit Colorants on Seed

A film coating was applied to 1 kg of corn seed according to Table 2, wherein the agricultural formulation, water, binder and colorant are combined to form colored seed coating compositions. A slurry of the components was made and applied to corn seed using an Aginnovation Rotary 12 Seed Coater. The treatment was applied over 5 seconds to the corn seeds in the spinning bowl. The seeds were allowed to dwell in the treater an additional 20-30 seconds, then ejected from the bowl and collected.

TABLE 2

| Colored Coating Compositions | | | |
|---|---|---|---|
| Component | Colored Coating A | Colored Coating B | Colored Coating C |
| Cruiser ® 5FS[1] | 3.1 g | 3.1 g | 3.1 g |
| Maxim ® Quattro[2] | 0.54 g | 0.54 g | 0.54 g |
| Water | 3.9 g | 3.9 g | 3.9 g |
| Treating Solutions ™ Polymer 2103[3] | 2.7 g | 2.7 g | 2.7 g |
| Treating Solutions ™ Red 1048[4] | 0.6 g | — | — |

TABLE 2-continued

| Colored Coating Compositions | | | |
|---|---|---|---|
| Component | Colored Coating A | Colored Coating B | Colored Coating C |
| Inventive Example 1 | — | 0.3 g | — |
| Comparative Example 4 | — | — | 0.3 g |

[1] Seed treatment insecticide available from Syngenta, Greensboro, NC
[2] Seed treatment fungicide available from Syngenta, Greensboro, NC
[3] Seed treatment polymer formulation available from Milliken & Company, Spartanburg, SC
[4] Pigment dispersion of Pigment Red 48:2 available from Milliken & Company, Spartanburg, SC After curing for 24 hours, the samples in Table 2 were tested for color change using the test method described herein. Three seeds were taken from each of the treated samples from Table 2 and placed into separated plastic beakers. Approximately 10 mL of household vinegar (Publix Distilled White Vinegar, 5% acetic acid in water, pH=2.81) or water was added to each beaker, the seeds were swirled gently for about 10 seconds and any difference in color between the water and vinegar solutions was noted visually. Test results are provided in Table 3.

TABLE 3

| Anti-Counterfeiting Color Change On Seed | | |
|---|---|---|
| Colorant Formulation | Seeds placed into water | Seeds placed into vinegar |
| Color Coating A | No color transferred to water | No color transferred to vinegar |
| Color Coating B | Red solution | Violet solution |
| Color Coating C | Red solution | Red solution |

The test results in Table 3 illustrate that a visual cue was apparent when the seeds coated with the Inventive Example 1 were placed into water versus vinegar. The Comparative Examples, Color Coating A, containing a pigment and Color Coating C, containing a heterocyclic thiadiazole azo dye (which contains one sulfur and 2 nitrogen atoms in the heterocycle), did not show the color change when placed in water versus vinegar. Therefore, this method provides the seed purchaser/consumer with a visual cue that the seed is authentic.

Testing for Authenticity of a Colored Agricultural Formulation

Colored agricultural formulations were prepared by blending the components in Table 4 by weight percent. Specifically, the components were combined in a 20 mL scintillation vial and mixed using a vortex mixer until homogeneity of the formulation was achieved.

TABLE 4

| Colored Agricultural Formulations | | | | |
|---|---|---|---|---|
| Component | Agricultural Composition 1 | Agricultural Composition 2 | Agricultural Composition 3 | Agricultural Composition 4 |
| Poncho ® Votivo ®[5] | | | 90 | 97.5 |
| CruiserMaxx ® Vibrance ®[6] | 90 | 97.5 | | |
| Inventive Example 1 | | 2.5 | | 2.5 |
| Treating Solutions ™ Red 1048[7] | 10 | | 10 | |

[5] Seed treatment insecticide and biological seed treatment available from BASF, Florham Park, NJ
[6] Seed treatment insecticide and fungicide available from Syngenta, Greensboro, NC
[7] Pigment dispersion of Pigment Red 48:2 available from Milliken & Company, Spartanburg, SC 10 mg samples of the compositions from Table 4 were added to separate 20 mL scintillation vials. 10 mL of each of the diluents from Table 5 were added separately to the vials, swirled briefly (5 seconds), and the observed color was recorded in Table 5. The pH of the diluents was measured using an Oakton pH 150 Meter (available from Oakton Instruments, Vernon Hills, IL) and is also recorded in Table 5.

TABLE 5

| Anti-Counterfeiting Testing In Colored Agricultural Formulations | | | | | |
|---|---|---|---|---|---|
| Sample | Tap Water pH = 6.67 | Vinegar[8] pH = 2.81 | Toilet Bowl Cleaner[9] pH = 1.33 | 7-UP[10] pH = 3.59 | Lemonade[11] pH = 2.97 |
| Agricultural Composition 1 | Pink | Pink | Pink | Pink | Pink |
| Agricultural Composition 2 | Red | Violet | Violet | Red | Violet |
| Agricultural Composition 3 | Pink | Pink | Pink | Pink | Pink |
| Agricultural Composition 4 | Red | Violet | Violet | Red | Violet |

[8] Publix Distilled White Vinegar, 5% acetic acid in water
[9] Lysol Power Toilet Bowl Cleaner - diluted 1:9 with distilled water
[10] Lemon-Lime Soda manufactured by Keurig Dr. Pepper
[11] Publix Old-Fashioned Lemonade The test results in Table 5 illustrate that colored Agricultural Compositions 2 and 4, which contain Inventive Example 1 colorant, displayed a color change from red to violet upon exposure to common household ingredients with a pH measuring less than 3 (such as vinegar, lemonade and toilet bowl cleaner). In contrast, colored Agricultural Compositions 1 and 3, which contain Pigment Red 48:2, did not exhibit a color change. Thus, the inventive colorants can be used to authenticate an agricultural formulation via an easy to use test method with common household ingredients.

Without wishing to be bound by theory, it is believed that the amine present in red azo colorants containing a thiazole and/or benzothiazole ring system that does not contain electron-withdrawing groups on the heterocyclic ring system will become protonated at a pH of equal to or less than 3, thus shifting the shade of the observed dye to a higher lambda max. With this shift in maximum absorbance of the chromophore to a higher wavelength, the observed change in color will shift from a red to a violet color. With those colorants containing an electron-withdrawing group, the basicity of the heterocyclic nitrogen is reduced and the nitrogen group is not protonated, and thus the color of the chromophore does not change.

Additional experiments were performed with the colorant of Inventive Example 1 to show performance once applied to white wheat seeds. Coating formulations were prepared according to Table 6. A slurry of the components was made and applied to white wheat seeds using an Aginnovation Rotary 12 Seed Coater. The treatment was applied over 5 seconds to the white wheat seeds in the spinning bowl. The seeds were allowed to dwell in the treater an additional 20-30 seconds, then ejected from the bowl and collected.

TABLE 6

Seed Coating Formulations for White Wheat

| Component | W-1 | W-2 | W-3 | W-4 |
|---|---|---|---|---|
| Vibrance ® Flexi[12] | 5.0 g | 5.0 g | 5.0 g | 5.0 g |
| Water | 8.1 g | 8.1 g | 8.1 g | 8.1 g |
| Treating Solutions ™ Polymer 2103 | 0.5 g | 0.5 g | 0.5 g | 0.5 g |
| Inventive Example 1 | 0.3 g | 0.5 g | 0.7 g | |
| Treating Solutions ™ Red 1048 | | | | 0.5 g |
| Total Slurry | 13.9 g | 14.1 g | 14.3 g | 14.1 g |

[12] Seed treatment fungicide available from Syngenta, Greensboro, NC

The treated seeds from Table 6 were stored at 50-55% relative humidity and 68-72° C. for 48 hours before being tested for dust-off. Dust-off was run using a Heubach Dustmeter. The dust-off protocol required 200 g of seed. The Heubach Dustmeter settings were 40 rpms and 20 L/min of air flow for 5 minutes. The results are reported in grams of dust per 100,000 seeds. The test was repeated twice and an average of the two tests reported. Results are shown in Table 7.

TABLE 7

Dust-off Results for White Wheat

| Treatment Formulation | Dust-off (grams dust/100,000 seeds) |
|---|---|
| W-1 | 0.02 |
| W-2 | 0.02 |
| W-3 | 0.02 |
| W-4 | 0.05 |

As one can see from the results in Table 7, the use of the inventive red azo colorant shows an improvement of >50% reduction in the level of dust-off levels of all treatments relative to the pigment formulation.

Additional experiments were performed with the colorant of Inventive Example 1 to show performance once applied to corn seeds. Coating formulations were prepared according to Table 8. A slurry of the components was made and applied to corn seeds using an Aginnovation Rotary 12 Seed Coater. The treatment was applied over 5 seconds to the corn seeds in the spinning bowl. The seeds were allowed to dwell in the treater an additional 20-30 seconds, then ejected from the bowl and collected.

TABLE 8

Seed Coating Formulations for Corn

| Component | C-1 | C-2 | C-3 | C-4 |
|---|---|---|---|---|
| Cruiser ® 5FS | 5.0 g | 5.0 g | 5.0 g | 5.0 g |
| Water | 8.1 g | 8.1 g | 8.1 g | 8.1 g |
| Treating Solutions ™ Polymer 2103 | 4.5 g | 4.5 g | 4.5 g | 4.5 g |
| Inventive Example 1 | 0.4 g | 0.6 g | 0.8 g | |
| Treating Solutions ™ Red 1048 | | | | 0.8 g |
| Total Slurry | 18.0 g | 18.2 g | 18.4 g | 18.4 g |

The treated seeds from Table 8 were stored at 50-55% relative humidity and 68-72° C. for 48 hours before being tested for dust-off. Dust-off was run using a Heubach Dustmeter. The dust-off protocol required 200 g of seed. The Heubach Dustmeter settings were 40 rpms and 20 L/min of air flow for 5 minutes. The results are reported in grams of dust per 100,000 seeds. The test was repeated twice and an average of the two tests reported. Results are shown in Table 9.

TABLE 9

Dust-off Results for Corn

| Treatment Formulation | Dust-off (grams dust/100,000 seeds) |
|---|---|
| C-1 | 0.12 |
| C-2 | 0.12 |
| C-3 | 0.13 |
| C-4 | 0.28 |

As one can see from the results in Table 9, the use of the inventive red azo colorant shows an improvement of >50% reduction in the level of dust-off levels of all treatments relative to the pigment formulation. Thus, improvements in the quality of the seed coatings can be gained through the use of a colorant such as Inventive Example 1.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

We claim:

1. A method for determining the authenticity of a seed or an agricultural formulation comprising the following steps:
   (a) Providing a seed or an agricultural formulation that contains a red azo colorant represented by the following formula:

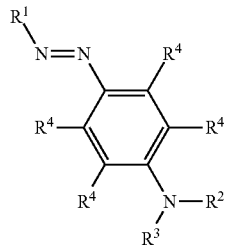

wherein $R^1$ is a heterocyclic group comprising at least one 5-membered ring incorporating one N and one S atom, and wherein the heterocyclic group is free from electron-withdrawing groups;
   $R^2$ and $R^3$ are independently selected from the group consisting of H, alkyl, and poly(oxyalkylene) moieties, wherein at least one of $R^2$ and $R^3$ is a poly(oxyalkylene) moiety; and
   $R^4$ is independently selected from the group consisting of H, alkyl, substituted alkyl, substituted nitrogen, hydroxyl, halogens and ethers;
   (b) Adding an acidic material to the seed or agricultural formulation of step "a;" and
   (c) Visually observing the occurrence of a color change from red to violet with the addition of the acidic material.

2. The method of claim 1, wherein the acidic material has a pH≤3.

3. The method of claim 1, wherein the seed of step "a" is in an aqueous solution prior to the addition of the acidic material.

4. The method of claim 1, wherein $R^1$ is selected from the group consisting of thiazole, isothiazole, benzisothiazole, and benzothiazole.

5. The method of claim 4, wherein $R^1$ is selected from thiazole and benzothiazole.

6. The method of claim 1, wherein $R^1$ includes one or more substituents on the 5-membered ring incorporating one N and one S atom selected from the group consisting of H, alkyl, substituted alkyl, hydroxyl, substituted hydroxyl, aryl, and substituted aryl.

7. The method of claim 1, wherein the poly(oxyalkylene) moieties are selected from ethylene oxide, propylene oxide, and butylene oxide, or combinations thereof.

8. The method of claim 1, wherein the total number of alkylene oxide residues per colorant molecule is in the range from 4 to 250.

9. The method of claim 1, wherein the total number of alkylene oxide residues per colorant molecule is in the range from 5 to 100.

10. The method of claim 1, wherein the total number of alkylene oxide residues per colorant molecule is in the range from 5 to 20.

11. The method of claim 1, wherein the red azo colorant of step "a" is present in an amount ranging from about 0.001% to about 50% by weight.

12. The method of claim 1, wherein the red azo colorant of step "a" is present in an amount ranging from about 0.5% to about 10% by weight.

13. The method of claim 1, wherein the red azo colorant of step "a" is represented by Formula I or Formula II:

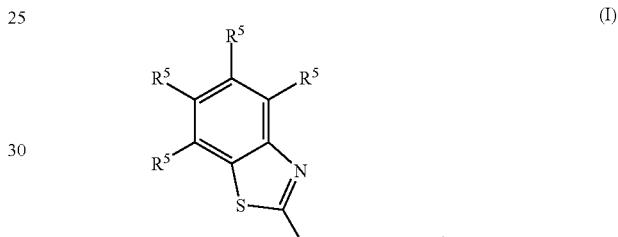

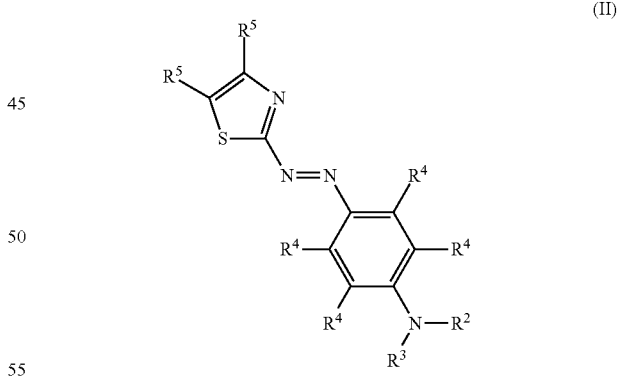

wherein
   $R^2$ and $R^3$ are independently selected from the group consisting of H, alkyl, and poly(oxyalkylene) moieties, and wherein at least one of $R^2$ and $R^3$ is a poly(oxyalkylene) moiety;
   $R^4$ is independently selected from the group consisting of H, alkyl, substituted alkyl, substituted nitrogen, hydroxyl, halogens and ethers; and
   $R^5$ is independently selected from the group consisting of H, alkyl, substituted alkyl, hydroxyl, substituted hydroxyl, aryl, and substituted aryl.

14. The method of claim 1, wherein the red azo colorant of step "a" is represented by Formula III:

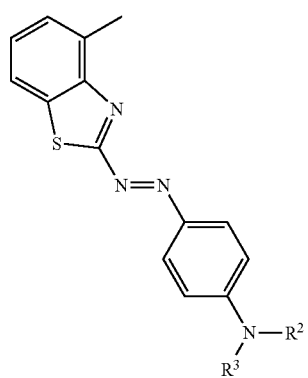

(III)

wherein $R^2$ and $R^3$ are independently selected from the group consisting of H, alkyl, and poly(oxyalkylene) moieties, and wherein at least one of $R^2$ and $R^3$ is a poly(oxyalkylene) moiety.

15. The method of claim 1, wherein the red azo colorant of step "a" is represented by Formula IV:

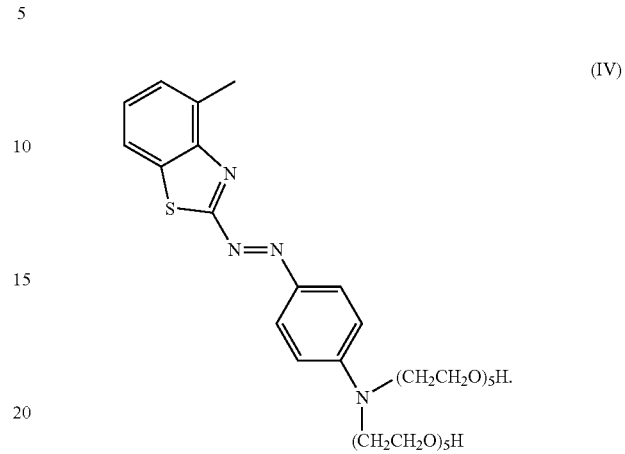

(IV)

* * * * *